United States Patent
Hermansson et al.

(10) Patent No.: US 7,959,618 B2
(45) Date of Patent: Jun. 14, 2011

(54) PANT-SHAPED ARTICLE WITH IMPROVED FIT

(75) Inventors: Sofia Hermansson, Västra Frölunda (SE); Catarina Linnér, Lindome (SE); Anna-Carin Elfström, Torslanda (SE); Jenny Hildeberg, Landvetter (SE)

(73) Assignee: SCA Hygiene Products AB, Gothenburg (SE)

( * ) Notice: Subject to any disclaimer, the term of this patent is extended or adjusted under 35 U.S.C. 154(b) by 262 days.

(21) Appl. No.: 10/792,895

(22) Filed: Mar. 5, 2004

(65) Prior Publication Data

US 2004/0225270 A1 Nov. 11, 2004

Related U.S. Application Data

(60) Provisional application No. 60/452,548, filed on Mar. 7, 2003.

(51) Int. Cl.
*A61F 13/15* (2006.01)
*A61F 13/20* (2006.01)
(52) U.S. Cl. ............... 604/385.01; 604/385.24
(58) Field of Classification Search .......... 604/378, 604/385.01, 385.24, 385.25, 383
See application file for complete search history.

(56) References Cited

U.S. PATENT DOCUMENTS

| | | | |
|---|---|---|---|
| 4,906,243 A | 3/1990 | Dravland | |
| 4,932,949 A * | 6/1990 | Thygesen et al. | 604/386 |
| 5,034,007 A | 7/1991 | Igaue et al. | |
| 5,624,420 A | 4/1997 | Bridges et al. | |
| 6,010,586 A | 1/2000 | Suprise | |
| 6,423,047 B1 * | 7/2002 | Webster | 604/385.15 |
| 6,607,515 B2 | 8/2003 | Glaug et al. | |
| 6,652,504 B1 | 11/2003 | Olson et al. | |
| 6,689,115 B1 | 2/2004 | Popp et al. | |
| 7,364,572 B2 | 4/2008 | Sandin et al. | |
| 2002/0068919 A1 * | 6/2002 | Shinohara et al. | 604/385.27 |
| 2002/0095127 A1 | 7/2002 | Fish et al. | |

(Continued)

FOREIGN PATENT DOCUMENTS

EP 0 351 389 A1 1/1990

(Continued)

OTHER PUBLICATIONS

English translation of specification of JP 09-111503 (English abstract provided by applicant).*

(Continued)

*Primary Examiner* — Melanie J Hand
(74) *Attorney, Agent, or Firm* — Buchanan Ingersoll & Rooney PC (57) ABSTRACT

A pant-shaped garment includes an outer panty having a length direction and a transverse direction and having a rear portion, a front portion, and a crotch portion. The garment includes a waist opening with a waist edge extending in the transverse direction and two leg openings each being bordered by a leg edge having a front part of the leg edge being located generally on the front portion and a rear part of the leg edge being located generally on the rear portion and on the crotch portion. The rear and front portions are mutually connected in two side joins running in the length direction from the waist opening to each leg opening. The front and rear portions of the outer panty substantially comprise an elastically extensible material. The rear part of each leg edge is curve-shaped and exhibits a concave curved segment located mainly on the rear portion.

36 Claims, 3 Drawing Sheets

U.S. PATENT DOCUMENTS

| | | | |
|---|---|---|---|
| 2002/0183712 A1* | 12/2002 | Datta et al. | 604/385.22 |
| 2003/0028165 A1* | 2/2003 | Curro et al. | 604/378 |
| 2008/0161767 A1 | 7/2008 | Sandin et al. | |

FOREIGN PATENT DOCUMENTS

| | | |
|---|---|---|
| EP | 716 587 | 6/1996 |
| EP | 0 761 194 A2 | 3/1997 |
| EP | 0 904 758 A2 | 3/1999 |
| EP | 1 106 154 A2 | 6/2001 |
| EP | 1 138 298 | 10/2001 |
| EP | 1 249 214 A2 | 10/2002 |
| JP | 58-73233 | 5/1983 |
| JP | 02029250 | 1/1990 |
| JP | 09111503 A | 4/1997 |
| JP | 10243961 A | 9/1998 |
| JP | 2001-276130 | 10/2001 |
| JP | 2002095699 A | 2/2002 |
| WO | WO 02/13747 | 2/2002 |

OTHER PUBLICATIONS

English translation of JP 09-111503 A to Ide.*
U.S. Appl. No. 10/793,277.
Sandin et al., Copending U.S. Appl. No. 12/073,658, filed Mar. 7, 2008 entitled "Pant-Shaped Article With Improved Fit".
Office Action dated Apr. 15, 2009 in Copending U.S. Appl. No. 12/073,658 to Hermansson et al. filed Mar. 7, 2008.
Office Action dated Mar. 22, 2006 in U.S. Appl. No. 10/793,277 to Sandin et al. filed Mar. 5, 2004 (US 7,364,572).
Office Action dated Sep. 18, 2006 in U.S. Appl. No. 10/793,277 Sandin et al. filed Mar. 5, 2004 (US 7,364,572).
Office Action dated Mar. 23, 2007 in U.S. Appl. No. 10/793,277 Sandin et al. filed Mar. 5, 2004 (US 7,364,572).
Office Action dated Sep. 13, 2007 in U.S. Appl. No. 10/793,277 Sandin et al. filed Mar. 5, 2004 (US 7,364,572).
Notice of Reasons for Rejection issued Dec. 18, 2009 in JP 2006-507923, and translation thereof.

* cited by examiner

PANT-SHAPED ARTICLE WITH IMPROVED FIT

CROSS-REFERENCE TO RELATED APPLICATIONS

The present application claims the benefit of U.S. Provisional Application No. 60/452,548, filed in the United States on Mar. 7, 2003, the entire contents of which are hereby incorporated herein by reference.

BACKGROUND OF THE APPLICATION

1. Technical Field

The invention pertains to a pant-shaped garment in the form of a pant diaper, a sanitary panty or an underpant comprising an outer panty having a length direction and a transverse direction and which exhibits a rear portion intended to be arranged over the buttocks of a user during use, a front portion intended to be arranged over the belly of a user during use, and a crotch portion intended to be arranged in the user's crotch during use. The pant-shaped garment further comprises a waist opening with a waist edge extending in the transverse direction and two leg openings each being bordered by a leg edge having a front part of the leg edge being located generally on the front portion and a rear part of the leg edge being located generally on the rear portion and on the crotch portion. The rear portion and the front portion are mutually connected in two side joins which run in the length direction from the waist opening to each leg opening.

2. Background Art

It has become increasingly more common to manufacture incontinence protectors in the form of pant diapers. Such pant diapers consist of an outer panty having an integral absorbent inner part. Alternatively, an outer panty can be used together with a separate incontinence shield which is temporarily attached inside the outer panty and which, thus, can be changed for a new incontinence shield while retaining the same outer panty. Both kinds of incontinence protectors are manufactured for infants as well as for incontinent adult persons. Sanitary panties are provided for use in connection with menstruation. Such sanitary panties are available with or without an integrated absorbent portion.

The pants concerned here are of the disposable kind, implying that the pant is intended to be discarded after use and not washed or otherwise restored for use. This means that the materials and production methods available are those which are cost-efficient and which do not result in exceedingly high-priced articles.

Particularly when the panty is intended for use by adult users, it is important that the panty as much as possible imitates a conventional textile underpant. Accordingly, the panty should be flexible, discreet and conformable and give a "textile" and tailored impression.

However, a special requirement for pant diapers and underpants intended for use in connection with incontinence and menstruation is that they must have a good fit and conform tightly to the waist and thighs of the user to prevent leakage of body fluids. In order to achieve such sealing, pant diapers, sanitary panties and underpants are provided with elastic elements in the form of bands or threads that are arranged around the waist opening and around the leg openings. However, there exists a risk of chafing and unpleasant pressure from tightly fitting elastic elements and wrinkled leg edges. In order to avoid the formation of gaps between the elastic elements and the body of the user and to prevent the leg edges from sliding up over the buttocks of the user, the elastic elements are often arranged with more pre-stretching than would have been necessary if the panty had a better fit.

Consequently, there still remains a need for a well-fitting and comfortable article in the form of a pant diaper, a sanitary panty or an underpant that affords good protection against leakage of body fluids at the leg openings.

OBJECTS AND SUMMARY

In accordance with embodiments of the invention, a garment of the kind desired in the introduction has been provided, which substantially removes the problems related to previously known garments.

The garment in accordance with embodiments of the invention comprise a front portion and a rear portion of the outer panty substantially comprising an elastically extensible material and by the rear part of each leg edge being curve-shaped and exhibiting a convex curved segment located mainly on the rear portion.

A panty having a leg cut in accordance with the invention has a very good fit and provides good shaping of the panty around the legs of the user. The panty conforms particularly well to the rear side of the thighs beneath the buttocks of the user and will not slide up on the user's buttocks.

In one embodiment, the rear part of the leg edge may advantageously have an S-shaped curvature. In such an instance, the leg edge has a slight S-shape. Alternatively, the part of the convexly curved part of the leg edge which is located rearmost can be generally straight.

In accordance with one embodiment of the invention, the front part of the leg edge is also curved and exhibits a concave curved shape. Such a concave curve shape conforms to the curvature on the front of the user's thighs and contributes to giving the panty a good fit.

In one embodiment, the crotch portion of the outer panty may comprise a substantially non-elastic material which is joined to the elastic front portion in a front join and to the elastic rear portion in a rear join, wherein both joins are arranged in the transverse direction of the outer panty. By arranging a non-stretchable, non-elastic material in the crotch portion a better support for attaching an absorbent unit in the crotch portion is obtained. Absorbent bodies are usually non-elastic and tend to break if they are exposed to stretching. It can therefore be desirable to minimize the stretching forces that such bodies are exposed to. Moreover, a non-elastic material is generally cheaper than elastic materials, implying that a non-elastic crotch portion involves cost savings that are particularly advantageous for disposable articles.

In order that the non-stretchable crotch portion will affect the ability of the outer panty to adapt its shape to the body of a user to as small a degree as possible, in some embodiments, the join between the non-elastic material in the crotch portion and the elastic material in the rear portion may be located at a level with or in front of the curve maximum of the convexly curved part of the leg edge. The expression curve maximum denotes the point on the rear part of the leg edge where the convex curvature is greatest.

In a corresponding manner, in some embodiments, the join between the non-elastic material in the crotch portion and the elastic material in the front portion may be located at a level with the point on the front part of the leg edge which is located furthest from the waist edge. This point is in general located on a transverse line dividing the front portion from the crotch portion and will be placed in the groin of the user when the pant diaper or diaper pant is put on.

In one embodiment, a particularly suitable material for the front portion and the rear portion of the outer panty may comprise an elastic and breathable laminate comprising two nonwoven layers and an elastic, perforated plastic film arranged between the nonwoven layers.

When the panty is a pant diaper or is intended for catamenial protection, it may comprise an absorbent unit, wherein the absorbent unit comprises an absorption core enclosed between a liquid permeable inner layer and a liquid impermeable barrier layer, and is arranged at least in the crotch portion of the outer panty.

In accordance with an embodiment of the invention, elastic elements are arranged along the rear part of the leg edge. Thus, an elongated elastic element is arranged with pre-stretching along preferably all of the rear part of the leg edge of each leg opening. By choosing a material for the front portion which is elastically extensible but which has a lower resistance to stretching than the elongated elastic elements, the elastic elements will constrict the rear portion of the leg edge and thereby stretch the elastic material along the front part of the leg edge. Thereby, the side joins will exhibit a curvature in a direction towards the rear portion and having a degree of curvature which increases in a direction from the waist opening towards the leg opening.

By means of the combination of an elastically stretchable material in the front portion and an elastic element arranged in a pre-stretched state along the rear leg edges of the leg openings, several advantages are obtained. Thus, the rear elastic element constricts the rear leg edge and also exerts a pulling force on the material in the front portion. The force is directed generally in the continuation of the rear elastic element, whereby the main stretching takes place in the front leg edge of each leg opening with the stretching gradually diminishing in a direction towards the waist edge. This implies that the side joins of the pant diaper or the underpant are pulled rearwards on the garment and take the form of a hook or a J. This shaping contributes to enhance the effect of the leg cut out and to improve the fit over the buttocks of the user. In addition, the curving of the side joins is favorable because the side joins will thereby during use be arranged behind the hip bone of the user, so that the risk of chafing and pressure on the hip bone is eliminated. Moreover, the pant diaper or the underpant acquires an extraordinarily good fit, closely conforming to the user's body shape. It is further an advantage to be able to exclude the use of an elastic element along the front leg edge of the leg openings. This affords a softer and more comfortable leg edge with minimal risk of chafing and uncomfortable pressure and brings about production advantages since it saves material and one production step.

Despite the absence of an elastic element along the front leg edges, the panty has a very good fit and provides adequate gasketing around the legs of the user. This is due to the elastic elements along the rear leg edges stretching and activating the elastic material in the front portion, whereby an elastically constricting force arises also in the front leg edges when the pant diaper or underpant is being worn. In one embodiment, because all of the front portion is elastically stretchable and the degree of stretching caused by the rear elastic element diminishes in a direction towards the waist edge, the elastic seal along the front edges of the leg openings becomes soft and comfortable without wrinkles or other irregularities. A conventional elastic element in the form of a thread or a band which is arranged along the front leg edge exerts a very localized pressure and will, in addition, wrinkle the material in the panty in a way which may give rise to chafing creases.

A further advantage with arranging elastic elements along the rear leg edges is that the rear elastic elements in an elegant manner pass over to the side joins, giving an attractive and tailored impression. Particularly for adult users of incontinence protectors, it is important that the incontinence protectors as much as possible imitate ordinary underwear and that the impression of a "diaper" is toned down.

BRIEF DESCRIPTION OF DRAWINGS

Embodiments of the invention will be described more closely with reference to the figures which are shown in the appended drawings.

DETAILED DESCRIPTION OF THE PREFERRED EMBODIMENTS

Figure 1:
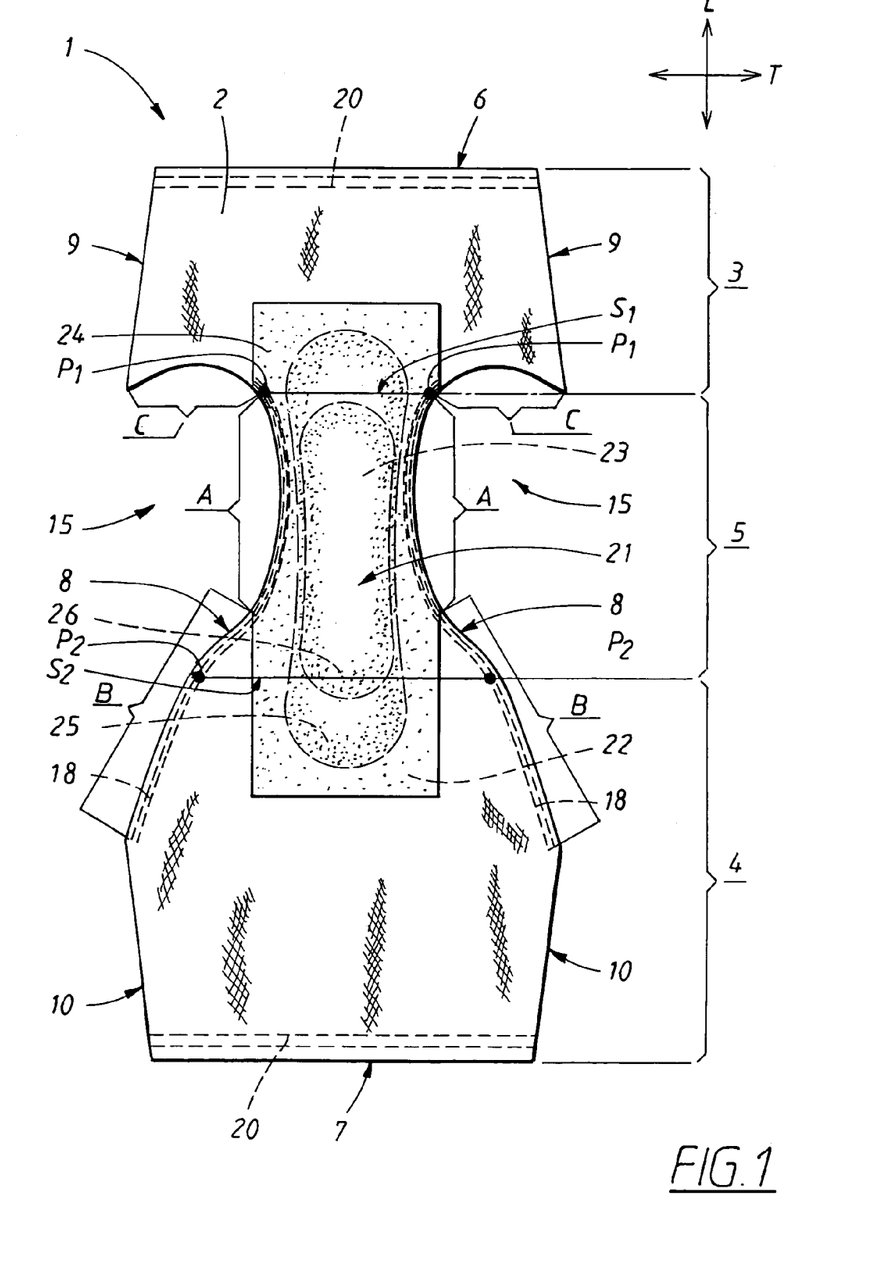
FIG. 1 a planar view of a pant diaper in accordance with an embodiment of the invention, seen from the side facing the user during use.
Figure 2:
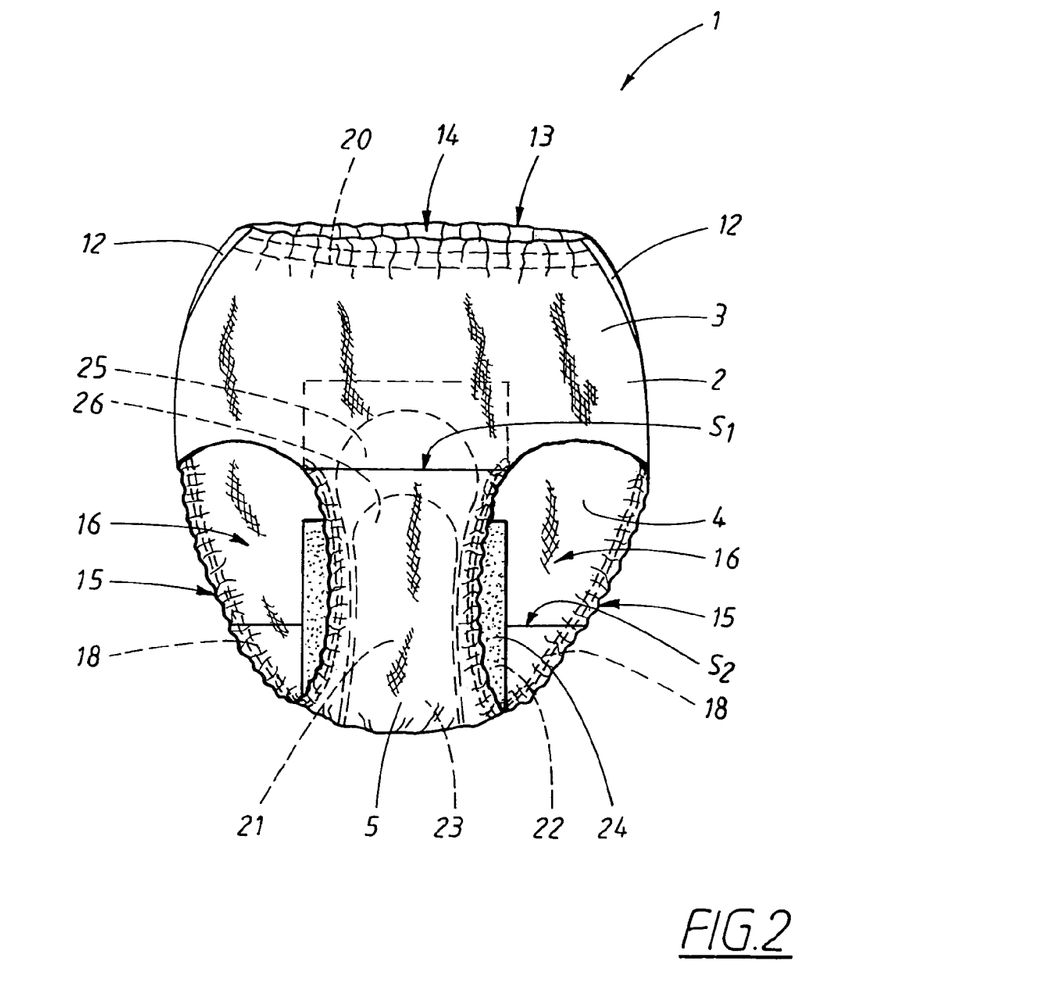
FIG. 2 a frontal view of the pant diaper in FIG. 1, as it appears in an assembled state.

For the sake of clarity, the pant diaper 1 in FIG. 1 is shown in a not fully-assembled, planar extended state. The pant diaper 1 has an elongated shape with a length direction L and a transverse direction T. In FIG. 2, the pant diaper 1 is shown as it appears in an assembled state and without being exposed to stretching forces. The pant diaper comprises an outer panty 2 which can be divided into a front portion 3, which during use is intended to be facing to the front of the user and to be arranged over the stomach of the user, a rear portion 4 which during use is intended to be facing rearwards on the user and to be arranged over the buttocks of the user and a crotch portion 5 located between the front portion 3 and the rear portion 4 and which is intended to be placed in the user's crotch during use.

In the extended state shown in FIG. 1, the pant diaper 1 has a straight front end edge or front edge 6, a straight rear end edge or back edge 7 and two side edges 8 which each exhibit a front and a rear straight side segment 9, 10, and a curved leg segment 15 located between the straight side segments 9, 10. In the shown embodiment, the curved leg segments or leg edges 15 have essentially the shape of a fishing hook with the hook part turned towards the front portion 3 of the pant diaper. The shape of the curved leg edges 15 is beneficial to the fit of the pant diaper. Thus, it is particularly beneficial that the rear part of each leg edge 15 be designed in a correct manner. As appears from FIG. 1, the rear part of the leg edge 15 of the pant diaper 1 has a concavely curved segment A, which is located in the crotch portion 5 of the pant diaper and a segment B which extends over the rear portion 4 and a little way in towards the crotch portion 5 and which exhibits a convex curvature. In the shown example, the rearmost part of the segment B is substantially straight. However, it is alternatively possible to design this part with a slight concave curvature so that the entire segment B is slightly S-shaped. By shaping the leg edge in accordance with an embodiment of the invention, the assembled pant diaper is given an exceptionally good fit that brings about a particularly good seal beneath the buttocks of the user.

Further, the leg edge 15 has a front segment C which is concavely curved in order to provide a better fit on the front side of the user's thighs.

In an assembled state as shown in FIG. 2, the front side segment 9 of each side edge 8 is joined to the corresponding rear side segment in a side join 12. Thereby, the front edge 6 and the back edge 7 form a waist edge 13 which surrounds a waist opening 14 and the curved leg edges 15 of the side edges 8 surround leg openings 16.

The side joins 12 are preferably made in a way to resist the pulling forces which arise when putting on and using the pant diaper but so that they can be torn apart when removing the used absorbent panty. An openable side join 12 does not have a greater cohesive ability than to allow the join to break at a lower force than that which is required to tear the surrounding material in the absorbent panty. The side joins 12 can be made, e.g., by welding or by adhesive.

The front portion 3 and the rear portion 4 of the outer panty 2 may be formed from an elastically stretchable material. Suitable elastic materials are different types of elastic nonwoven materials. An elastic nonwoven material for use in an absorbent panty in accordance with an embodiment of the invention is preferably elastically stretchable to at least 80% and preferably at least 100% in the transverse direction of the panty in order to provide sufficient elastic seal around the edges 15 of the leg openings 16 on the front portion 3. It is further advantageous if the elastic nonwoven material can be elastically stretched also in the length direction of the absorbent panty, i.e., in a direction perpendicular to the transverse direction.

The elastic sheet material in the outer panty 2 may comprise a laminate of two or more layers. In the example shown in FIG. 1, the front portion 3 and the rear portion 4 comprise elastic material while the crotch portion 5 comprises an essentially non-elastic material. Naturally, it is possible to manufacture the entire outer panty from elastic material. A material which is suitable for the purpose is a three-layer laminate with a nonwoven layer on each side of an apertured elastic film. Such a laminate provides an elastic and breathable outer panty. It is also possible to use other breathable elastic materials. For instance, so-called SMS-materials can be used. An SMS-material is a nonwoven laminate with a layer of spunbond nonwoven on each side of a meltblown nonwoven layer.

The crotch portion 5 of the outer panty 2 comprises an essentially non-elastic material which is joined to the elastic front portion 3 in a front join S1 and to the elastic rear portion 4 in a rear join S2, wherein the two joins S1, S2 are arranged in the transverse direction T of the outer panty 2.

In order that the non-elastic crotch portion 5 should have as little as possible negative effect on the ability of the outer panty to adapt its shape to the body of a user, the join S2 between the non-elastic material in the crotch portion 5 and the elastic material in the rear portion 4 may be located at a level with the curve maximum P2 on the convexly curved segment B of the leg edge. The expression curve maximum P2 denotes the point on the rear part of the leg edge 15 where the convex curvature is greatest. Accordingly, the rear join S2 runs in the transverse direction T between the curve maxima P2 on each convexly curved segment B of the leg edges 15.

In a corresponding way, the join S1 between the non-elastic material in the crotch portion 5 and the elastic material in the front portion 3 may be located at a level with the point P1 on the front segment C of the leg edge 15 which is located farthest from the waist edge. In general, this point may be positioned on a transverse line dividing the front portion 3 from the crotch portion 5 and will be located in the groin of the user when the pant diaper 1 is worn.

Elastic elements are arranged as leg elastic 18 around the leg openings 16 and as waist elastic 20 around the waist opening 14. When the outer panty 2 is formed from a laminate of two or more layers, the elastic elements 18, 20 are suitably attached between two such layers. The elastic elements 18 around the leg openings may be only arranged on the crotch portion 5 and the rear portion 4, while the segment C of the leg edges 15 which extends over the front portion 3 is free from special elastic elements. There may be more elastic elements 18 along the concavely curved segment A of the leg edge 15 than along the convexly curved segment B. Thereby, the constricting force is greater in the crotch portion 5 of the pant diaper. Such differentiated elastic can, of course, be accomplished by varying the tension in one and the same elastic element. However, it is not necessary for the invention that elastic with different constricting ability be arranged along the leg edges 15.

Since the outer panty 2 may comprise elastic material, it is not necessary to provide the waist opening 14 with special elastic elements 20, the elasticity in the outer panty 2 for many applications being sufficient for the diaper pant 2 to stay securely and comfortably in place and to fit tightly around the waist of the user.

The elastic elements in the leg elastic 18 and the waist elastic 20 can be in the form of elastic threads, bands or similar. If elastic threads or bands are used, two or more of these are often applied parallel with each other. The material can be rubber, elastic foam, etc.

A core package 21 is attached inside the elastically stretchable outer panty 2 for instance by means of adhesive or by welding. The core package 21 can be attached to the outer panty 2 over the entire common surface or only over parts thereof. However, the core package 21 is preferably sufficiently well anchored inside the outer panty 2 to avoid it coming away or being moved from its proper position during use.

The core package 21 comprises a liquid barrier layer 22, an absorbent core 23 and a liquid-permeable inner layer 24. The core package 21 is attached with the liquid barrier layer 22 against the outer panty 2. FIG. 1 shows an absorbent core 23 comprising two superposed absorbent layers 25, 26 wherein the lower absorbent layer 25, which is located closest to the liquid barrier layer 22, is somewhat larger than the upper absorbent layer 26, which is located closest to the inner layer 24. In the shown example, the core package 21 has an angular hour-glass shape in the plane, the planar shape of the core package being defined by the shape of the liquid barrier layer 22 and the liquid-permeable inner layer 24 which together enclose the absorbent core 23. Naturally, it is possible to use core packages 21 having a different planar shape. The liquid barrier layer 22 and the inner layer 24 may, for instance, have a more rounded hour-glass shape, a rectangular shape, a trapezoid shape, an oval shape, etc. Further, the core package 21 does not need to have the size shown in the Fig. Larger as well as smaller absorbent cores 23 can be used depending on the absorbent capacity desired in the pant diaper. Further, it is not necessary to arrange an absorbent core 23 in a special core package. Instead, the liquid barrier layer 22 and the liquid-permeable inner layer 24 may be integrated parts of the outer panty 2.

Because the material in the crotch portion 5 of the outer panty 2 may be non-stretchable and non-elastic, a better support is obtained for attaching the core package 21 in the crotch portion. Absorbent cores usually comprise non-elastic materials having fairly low coherency and tend to break if they are exposed to stretching. It may thus be desirable to minimize the stretching forces to which such cores are exposed.

The liquid permeable inner layer 24 may comprise any material known for the purpose such as layers of nonwoven material, perforated plastic film, netting, tow (parallel fibers), or similar. The inner layer 24 may, of course, also comprise a laminate of two or more layers of the same or different materials.

The liquid barrier layer 22 may comprise a liquid-impermeable plastic film, a hydrophobic nonwoven layer or a nonwoven layer which has been treated to have liquid barrier properties, or any other flexible material layer which has the ability to resist liquid penetration. However, it may be an advantage if the liquid barrier layer 22 exhibits a certain breathability, i.e., allows passage of water vapor through the layer 22.

The absorbent core 23 can be formed from absorbent materials such as cellulose fluff pulp, tissue, absorbent foam, etc. It is also common that the absorbent core 23 comprises superabsorbents, i.e., polymeric materials which can absorb body fluids corresponding to several times their own weight while forming an aqueous gel. Such superabsorbents usually exist in the form of particles, but fibers, flakes, granules and film are also found. In addition, the absorbent core 23 may comprise non-absorbent components such as stiffening elements, shaping elements, binders, etc. Different kinds of fluid receiving and fluid distributing structures such as fibrous wadding, open-cell foam, wicking layers or similar may also be included in the core package 21.

The different components which are included in the core package 21 may be connected to each other in a conventional manner, e.g., by gluing or welding with heat or ultrasonically. The core package 21 may comprise further components apart from those which have been described here, for instance the core package may comprise liquid transport layers, elastic elements, shape-stabilizing elements, shaping elements, or the like. Although the absorbent core has been shown having two absorbent layers 25, 26, alternative arrangements can be used. For instance, for some applications it may be sufficient with a single absorbent layer while other applications may require more than two absorbent layers. Thus, the design of the absorbent core can be adapted to the amount of liquid that the absorbent core is expected to absorb. Similarly, the kind of body fluids that are to be absorbed and the manner in which the body fluids are delivered to the absorbent core are naturally of importance for the size and properties of the absorbent core.

As has previously been mentioned, FIG. 2 shows how one embodiment of the pant diaper appears before it is put on. All elastic elements and components are substantially non-stretched. Because the leg elastic 18 and the waist elastic 20 are attached to the outer panty 2 in a stretched state, they contract the material in the outer panty 2 when the stretching ceases. This means that, before it is put on, the pant diaper 1 has a somewhat wrinkled waist edge 13 and leg edges 15 that are wrinkled in the crotch portion 5 and in the rear portion 4.

Figure 3:
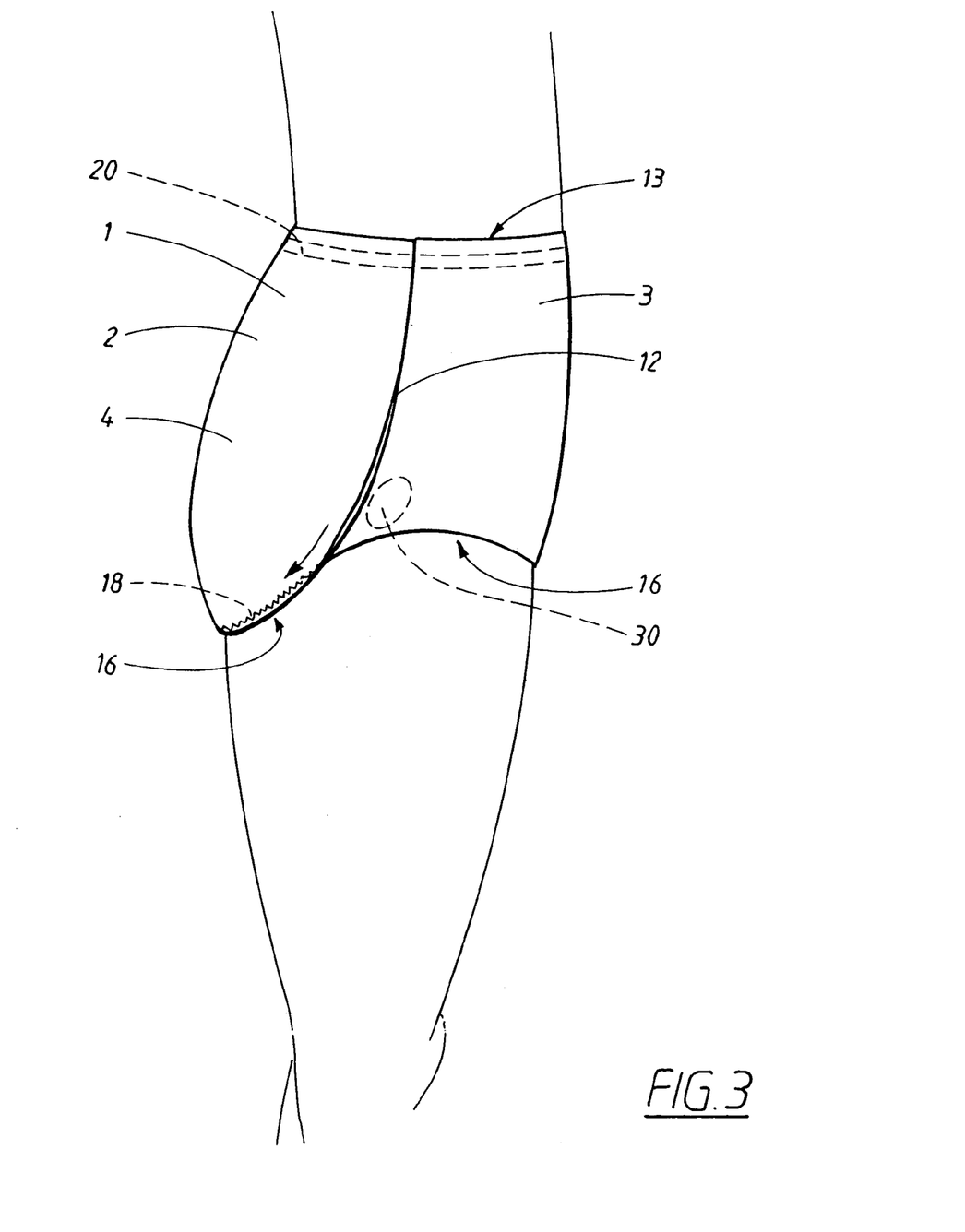
FIG. 3 a side view of the pant diaper in FIG. 1, as it appears during use.

In FIG. 3, an embodiment of the pant diaper 1 is shown while being worn by a user. Due to the tension in the leg elastic 18 along the leg edge 15 on the crotch portion 5 and the rear portion 4 being greater than the resistance to stretching in the elastic material of the outer panty 2 on the front portion 3, the part of the side join 12 which is located closest to the leg opening 16 is pulled rearwards on the pant diaper 1. Thereby, the side join 12 is given a curved shape with a curve radius which increases in a direction from the waist edge 13 towards the leg edge 15. The curving of the side join 12 results in the side join 12 being placed behind the hip bone 30 of the user when the pant diaper is put on. This is a major advantage since the risk of chafing and unpleasant pressure from the side join 12 is thereby eliminated. Furthermore, an overlap between the side join 12 and any side seams on a garment which is worn over the pant diaper 1 is avoided.

The absence of a particular elastic element along the leg edge 15 on the front portion 3 is advantageous from several aspects. Above all, it gives the pant diaper an exceptionally good fit with a smooth and comfortable seal around the front part of the user's thighs. The risk of chafing on the fronts and insides of the thighs is completely eliminated and the pant diaper can be discreetly worn under normal clothing.

The invention should not be regarded as being limited by the described embodiments. Accordingly, within the scope of the invention, it is possible to design the absorbent portion of the pant diaper in a different manner from that which has been described. The shape and size of the absorbent core, as well as the shape and size of the liquid barrier layer and the inner layer can, of course, be varied. It is also possible to completely exclude the liquid barrier layer. In such a case, it is generally suitable that the material in the pant diaper, at least within the area of the absorbent core, can resist liquid penetration.

Moreover, the leg elastics may be arranged only along, for instance, the part of the leg edge that extends over the rear portion or along the leg edge on the rear portion and a part of the crotch portion.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A pant-shaped garment having a length direction and a transverse direction, the garment comprising:
    a rear portion intended to be arranged over the buttocks of a user during use;
    a front portion intended to be arranged over the belly of a user during use;
    a crotch portion intended to be arranged in the user's crotch during use;
    a waist opening with a waist edge extending in the transverse direction; and
    two leg openings each being bordered by a leg edge wherein each leg edge has a front part of the leg edge being located generally on the front portion and a rear part of the leg edge being located generally on the rear portion;
    wherein the rear portion and the front portion are mutually connected in two side joins which run in the length direction from the waist opening to each leg opening;
    wherein the front portion and the rear portion of the garment are each comprised of an elastically extensible sheet material;
    wherein the rear part of each leg edge is curve-shaped and exhibits a convex curved segment with respect to the rear portion when the garment is in a flat outstretched state, wherein the convex curved segment is located mainly on the rear portion; and
    wherein the convex curved segment extends along essentially the entirety of each leg edge located in the rear portion of the garment,
    wherein the crotch portion is joined to the front portion in a front join and to the rear portion in a rear join, wherein both joins are arranged parallel to the transverse direction,
    wherein the front, crotch and rear portions are discontinuous panels prior to the joining.

2. The pant-shaped garment according to claim 1, wherein the front part of the leg edge has a concave curved shape.

3. The pant-shaped garment according to claim 1, wherein the rear part of the leg edge has an S-shaped curvature.

4. The pant-shaped garment according to claim 2, wherein the crotch portion comprises a substantially non-elastic material.

5. The pant-shaped garment according to claim 4, wherein the join between the non-elastic material in the crotch portion and the elastic material in the rear portion is located at a level with or in front of the point on the rear part of the leg edge where the convex curvature is greatest.

6. The pant-shaped garment according to claim 4, wherein the join between the non-elastic material in the crotch portion and the elastic material in the front portion is located at a level with a point on the front part of the leg edge which is located furthest from the waist edge.

7. A pant-shaped garment having a length direction and a transverse direction, the garment comprising:
   a rear portion intended to be arranged over the buttocks of a user during use;
   a front portion intended to be arranged over the belly of a user during use;
   a crotch portion intended to be arranged in the user's crotch during use;
   a waist opening with a waist edge extending in the transverse direction; and
   two leg openings each being bordered by a leg edge wherein each leg edge has a front part of the leg edge being located generally on the front portion and a rear part of the leg edge being located generally on the rear portion;
   wherein the rear portion and the front portion are mutually connected in two side loins which run in the length direction from the waist opening to each leg opening;
   wherein the front portion and the rear portion of the garment are each comprised of an elastically extensible sheet material;
   wherein the rear part of each leg edge is curve-shaped and exhibits a convex curved segment with respect to the rear portion when the garment is in a flat outstretched state, wherein the convex curved segment is located mainly on the rear portion; and
   wherein the convex curved segment extends along essentially the entirety of each leg edge located in the rear portion of the garment,
   wherein the front portion and the rear portion comprises an elastic laminate comprising two nonwoven layers and an elastic, perforated plastic film arranged between the nonwoven layers.

8. The pant-shaped garment according to claim 1, further comprising an absorbent package, wherein the absorbent package comprises an absorption core enclosed between a liquid-permeable inner layer and a liquid-impermeable barrier layer and is arranged at least in the crotch portion of the outer panty.

9. The pant-shaped garment according to claim 1, wherein elastic elements are arranged along the rear part of the leg edge.

10. A pant-shaped garment having a length direction and a transverse direction, the garment comprising:
    a rear portion intended to be arranged over the buttocks of a user during use;
    a front portion intended to be arranged over the belly of a user during use;
    a crotch portion intended to be arranged in the user's crotch during use;
    a waist opening with a waist edge extending in the transverse direction; and
    two leg openings each being bordered by a leg edge wherein each leg edge has a front part of the leg edge being located generally on the front portion and a rear part of the leg edge being located generally on the rear portion;
    wherein the rear portion and the front portion are mutually connected in two side loins which run in the length direction from the waist opening to each leg opening;
    wherein the front portion and the rear portion of the garment are each comprised of an elastically extensible sheet material;
    wherein the rear part of each leg edge is curve-shaped and exhibits a convex curved segment with respect to the rear portion when the garment is in a flat outstretched state, wherein the convex curved segment is located mainly on the rear portion; and
    wherein the convex curved segment extends along essentially the entirety of each leg edge located in the rear portion of the garment,
    wherein the front portion and the rear portion consist of an elastically extensible material.

11. The pant-shaped garment according to claim 4, wherein the crotch portion of the outer panty consists of a substantially non-elastic material.

12. The pant-shaped garment according to claim 7, wherein the front portion and the rear portion of the outer panty consist of an elastic laminate having two nonwoven layers and an elastic, perforated plastic film arranged between the nonwoven layers.

13. The garment according to claim 1, wherein each leg edge includes a crotch part located on the crotch portion.

14. The garment according to claim 1, wherein the crotch portion is non-stretchable and the join between the crotch portion and the elastic material in the rear portion should be located at a level with or in front of the point on the rear part of the leg edge where the convex curvature is greatest.

15. A pant shaped garment having a length direction and a transverse direction, the garment comprising
    a rear portion intended to be arranged over the buttocks of a user during use,
    a front portion intended to be arranged over the belly of a user during use,
    a nonelastic crotch portion intended to be arranged in the user's crotch during use and,
    a waist opening with a waist edge extending in the transverse direction and two leg openings each being bordered by a leg edge having at least a front part of the leg edge being located generally on the front portion and a rear part of the leg edge being located generally on the rear portion and on the crotch portion,
    wherein the front, crotch and rear portions are discontinuous panels prior to the joining,
    wherein the rear portion and the front portion are mutually connected in two side joins which run in the length direction from the waist opening to each leg opening,
    wherein the front portion and the rear portion of the garment consist substantially of elastically extensible material and the rear part of each leg edge is curve-shaped and has a convex curved segment with respect to the rear portion when the garment is in a flat outstretched state, wherein the convex curved segment is located mainly on the rear portion, and
    wherein the convex curved segment extends along essentially the entirety of each leg edge located in the rear portion of the garment.

16. The garment according to claim 15, wherein the front part of the leg edge which is located on the front portion has a concave curved shape.

17. The garment according to claim 15, wherein the rear part of the leg edge has an S-shaped curvature.

18. The garment according to claim 16, wherein the crotch portion is joined to the front portion in a front join and to the rear portion in a rear join, wherein both joins are arranged parallel to the transverse direction.

19. The garment according to claim 18, wherein the join between the non-elastic material in the crotch portion and the elastic material in the rear portion is located at a level with or in front of the point on the rear part of the leg edge where the convex curvature is greatest.

20. The garment according to claim 15, wherein the front portion and the rear portion include an elastic laminate comprising two nonwoven layers and an elastic, perforated plastic film arranged between the nonwoven layers.

21. The garment according to claim 15, further comprising an absorbent package, wherein the absorbent package comprises an absorption core enclosed between a liquid permeable inner layer and a liquid impermeable barrier layer and is arranged at least in the crotch portion of the outer panty.

22. The garment according to claim 15, wherein the crotch portion is non-stretchable and the join between the crotch portion and the elastic material in the rear portion should be located at a level with or in front of the point on the rear part of the leg edge where the convex curvature is greatest.

23. A pant-shaped garment having a length direction and a transverse direction, the garment comprising:
a rear portion intended to be arranged over the buttocks of a user during use;
a front portion intended to be arranged over the belly of a user during use;
a crotch portion intended to be arranged in the user's crotch during use, wherein the crotch portion comprises a substantially non-elastic material which is joined to the elastic front portion in a front join and to the elastic rear portion in a rear join, wherein both joins are arranged parallel the transverse direction, wherein the front, crotch and rear portions are discontinuous panels prior to the joining;
a waist opening with a waist edge extending in the transverse direction; and
two leg openings each being bordered by a leg edge wherein each leg edge has a front part of the leg edge being located generally on the front portion and a rear part of the leg edge being located generally on the rear portion; and
an absorbent core package attached to an inside of the garment at least in the crotch portion;
wherein the rear portion and the front portion are mutually connected in two side joins which run in the length direction from the waist opening to each leg opening;
wherein the front portion and the rear portion of the garment are each comprised of an elastically extensible sheet material;
wherein the rear part of each leg edge is curve-shaped and exhibits a convex curved segment with respect to the rear portion when the garment is in a flat outstretched state, wherein the convex curved segment is located mainly on the rear portion; and
wherein the convex curved segment extends along essentially the entirety of each leg edge located in the rear portion of the garment.

24. The pant-shaped garment according to claim 1, wherein the elastically extensible material is stretchable to at least 80% in the transverse direction.

25. The pant-shaped garment according to claim 16, wherein the elastically extensible material is stretchable to at least 80% in the transverse direction.

26. The pant-shaped garment according to claim 23, wherein the elastically extensible material is stretchable to at least 80% in the transverse direction.

27. A pant-shaped garment having a length direction and a transverse direction, the garment comprising:
a panty including a rear portion intended to be arranged over the buttocks of a user during use, a front portion intended to be arranged over the belly of a user during use, a crotch portion intended to be arranged in the user's crotch during use, wherein the crotch portion comprises a substantially non-elastic material which is joined to the elastic front portion in a front join and to the elastic rear portion in a rear join, wherein both joins are arranged parallel to the transverse direction, wherein the front, crotch and rear portions are discontinuous panels prior to the joining, a waist opening with a waist edge extending in the transverse direction; and two leg openings each being bordered by a leg edge wherein each leg edge has a front part of the leg edge being located generally on the front portion and a rear part of the leg edge being located generally on the rear portion;
wherein the rear portion and the front portion are each comprised of an elastically extensible sheet material and are mutually connected in two side joins which run in the length direction from the waist opening to each leg opening;
an absorbent core package attached to an inside of the panty at least in the crotch portion;
wherein the rear part of each leg edge is curve-shaped and exhibits a convex curved segment with respect to the rear portion, wherein the convex curved segment is located mainly on the rear portion; and wherein the point on the rear part of the leg edge where the convex curvature is greatest is adjacent the join between the non-elastic material in the crotch portion and the elastic material in the rear portion or behind the join; and
wherein the convex curved segment extends along essentially the entirety of each leg edge located in the rear portion of the garment.

28. The pant-shaped garment according to claim 1, wherein the rear portion extends outwardly at the convex curved segment.

29. The pant-shaped garment according to claim 1, wherein elastic elements are arranged along the convex curved segment.

30. The garment according to claim 15, wherein elastic elements are arranged along the convex curved segment.

31. The pant-shaped garment according to claim 1, wherein the side joins which run in the length direction from the waist opening to each leg opening are adapted such that opening of a side join results in permanent deformation or rupture.

32. The pant-shaped garment according to claim 15, wherein the side joins which run in the length direction from the waist opening to each leg opening are adapted such that opening of a side join results in permanent deformation or rupture.

33. A pant-shaped garment having a length direction and a transverse direction, the garment comprising:
a rear portion intended to be arranged over the buttocks of a user during use;
a front portion intended to be arranged over the belly of a user during use;
a crotch portion intended to be arranged in the user's crotch during use;
a waist opening with a waist edge extending in the transverse direction; and
two leg openings each being bordered by a leg edge wherein each leg edge has a front part of the leg edge being located generally on the front portion and a rear part of the leg edge being located generally on the rear portion;
wherein the rear portion and the front portion are mutually connected in two side loins which run in the length direction from the waist opening to each leg opening;
wherein the front portion and the rear portion of the garment are each comprised of an elastically extensible sheet material;
wherein the rear part of each leg edge is curve-shaped and exhibits a convex curved segment with respect to the rear portion when the garment is in a flat outstretched state, wherein the convex curved segment is located mainly on the rear portion; and
wherein the convex curved segment extends along essentially the entirety of each leg edge located in the rear portion of the garment,
wherein the side joins which run in the length direction from the waist opening to each leg opening are formed by welding or permanent adhesive from the waist opening to each leg opening.

34. The pant-shaped garment according to claim 15, wherein the side joins which run in the length direction from the waist opening to each leg opening are formed by welding or permanent adhesive from the waist opening to each leg opening.

35. The pant-shaped garment according to claim 1, wherein the convex curved segment continues to extend along a part of each leg edge located in the crotch portion of the garment located adjacent to each leg edge located in the rear portion of the garment.

36. The pant-shaped garment according to claim 15, wherein the convex curved segment continues to extend along a part of each leg edge located in the crotch portion of the garment adjacent to each leg edge located in the rear portion of the garment.

* * * * *